US012616648B2

(12) United States Patent (10) Patent No.: US 12,616,648 B2
Lambert et al. (45) Date of Patent: May 5, 2026

(54) COSMETIC COMPOSITION

(71) Applicant: GIVAUDAN SA, Vernier (CH)

(72) Inventors: Carole Lambert, Cugnaux (FR); Romain Reynaud, Reims (FR)

(73) Assignee: GIVAUDAN SA, Vernier (CH)

( * ) Notice: Subject to any disclaimer, the term of this patent is extended or adjusted under 35 U.S.C. 154(b) by 190 days.

(21) Appl. No.: 16/980,061

(22) PCT Filed: Apr. 8, 2019

(86) PCT No.: PCT/EP2019/058826
§ 371 (c)(1),
(2) Date: Sep. 11, 2020

(87) PCT Pub. No.: WO2019/193203
PCT Pub. Date: Oct. 10, 2019

(65) Prior Publication Data
US 2021/0015735 A1 Jan. 21, 2021

(30) Foreign Application Priority Data

Apr. 6, 2018 (GB) ...................................... 1805780

(51) Int. Cl.
| | |
|---|---|
| *A61K 36/00* | (2006.01) |
| *A61K 8/9789* | (2017.01) |
| *A61Q 19/00* | (2006.01) |
| *A61Q 19/08* | (2006.01) |

(52) U.S. Cl.
CPC .......... *A61K 8/9789* (2017.08); *A61Q 19/007* (2013.01); *A61Q 19/08* (2013.01)

(58) Field of Classification Search
None
See application file for complete search history.

(56) References Cited

FOREIGN PATENT DOCUMENTS

| | | |
|---|---|---|
| CN | 102961282 A | 3/2013 |
| CN | 104415089 A | 3/2015 |
| CN | 104523473 A | 4/2015 |
| CN | 102462653 A | 5/2015 |
| EP | 1136062 A1 | 9/2001 |
| FR | 2890860 A1 | 3/2007 |
| JP | 02187498 A * | 7/1990 |
| JP | H02187498 A | 7/1990 |
| JP | 104248900 A | 9/1992 |
| JP | 2000229804 A | 8/2000 |
| JP | 2001213754 A | 8/2001 |
| KR | 20100071652 A | 6/2010 |
| RU | 2528693 C1 | 9/2014 |
| WO | 2016144196 A1 | 9/2016 |

OTHER PUBLICATIONS

Adam et al. (2014) J. Chem. Eng. Data 59: 183-188. (Year: 2014).*
Swamy et al. (2015) Molecules 20: 8521-8547. (Year: 2015).*
International Search Report and Written Opinion of the International Searching Authority for corresponding application PCT/EP2019/055722 dated Jun. 26, 2019.
GB Search Report for corresponding application GB 1804011.3 dated Oct. 15, 2018.
Mcmahon Christopher: "Patchouli", Internet Citation, Jan. 24, 2001, USA.
Anonymous: "Super Hydrating Body Balm", Database GNPD [Online] MINTEL; Aug. 11, 2015, retrieved from www. gnpd.com.
Anonymous: "Calendula Shampoo", Database GNPD [Online] Mintel; Mar. 20, 2017; retrieved from www,gnpd,com.
Phakawat Tongnuanchan, et al: "Essential Oils: Extraction, Bioactivities, and Their Uses for Food Preservation", Journal of Food Science, vol. 79; No. 7, Jul. 2, 2014, pp. R1231-R1249.
Swamy, et al.: "A Comprehensive Review on the Phytochemical Constituents and Pharmacological Activities of Pogostemon cablin Benth.: An Aromatic Medicinal Plant of Industrial Importance", Molecules, 2015, 20, pp. 8521-8547; doi:10.3390/molecules20058521.
Van Beek T.A., et al.: "The essential oil of patchouli, Pogostemon cablin: A review", Flavour and Fragrance Journal, 33(1), 2017, p. 6-51.
Wang, D., et al.: "Nonvolatile chemical constituents from Pogostemon cablin". Department of Phytochemistry, China Pharmaceutical University, China, Páginas, 2704-2707, 2010.
Hain Celestial Group, USA, Treatment Shampoo, ID#2452257, Mintel GNPD [online], 2014.05, [Search date: Jan. 12, 2023].
The Refinery, UK, Shave Oil, ID#599730, Mintel GNPD [online], Oct. 2006, [Search date: Jan. 12, 2023].

* cited by examiner

*Primary Examiner* — Russell G Fiebig
(74) *Attorney, Agent, or Firm* — Norris McLaughlin, PA

(57) ABSTRACT

A cosmetic composition is provided, which comprises a carrier and a Patchouli stem extract, in particular an extract from exhausted Patchouli stems. This composition provides anti-oxidant, anti-elastase, anti-hyaluronase, and anti-tyrosinase activities.

7 Claims, No Drawings

COSMETIC COMPOSITION

This is an application filed under 35 USC 371 based on PCT/EP2019/058826, filed 8 Apr. 2019, which in turn is based on GB 1805780.2, filed 6 Apr. 2018. The present application claims the full priority benefit of these prior applications and herein incorporates by reference the full disclosures of these prior applications.

The present invention relates to cosmetic compositions comprising a Patchouli stem extract.

Patchouli (*Pogostemon cablin*) is a species of plant from the family Lamiaceae, commonly called the "mint" or "deadnettle" family. The plant grows as a bushy herb, with erect stems reaching around 75 cm in height and bearing small, pale pink-white flowers. It is native to tropical regions of Asia.

The heavy and strong scent of patchouli has been used for centuries in perfumes and, more recently, in incense, insect repellents, and alternative medicines. *Pogostemon cablin*, among other members of the *Pogostemon* genus, is commonly cultivated for its essential oil, known as patchouli oil. Patchouli grows well in warm to tropical climates. The seed-producing flowers are very fragrant and blossom in late fall. The tiny seeds may be harvested for planting, but they are very delicate and easily crushed. Cuttings from the mother plant can also be rooted in water to produce additional plants.

Extraction of Patchouli's essential oil is typically achieved by steam distillation of the dried leaves and stems, requiring rupture of its cell walls by steam scalding, light fermentation, or drying. Leaves may be harvested several times a year and, when dried, may be exported for distillation.

The main chemical component of patchouli oil is patchoulol, a sesquiterpene alcohol. Other important components include Germacrene-B, and Norpatchoulenol. Overall, around 140 chemicals have been identified in Patchouli (Swamy et al. in Molecules 2015, 20, 8521-8547) including terpenoids, phytosterols, flavonoids, organic acids, lignins, alkaloids, glycosides, alcohols, and aldehydes. The volatiles are mainly composed of patchouli alcohol, $\alpha$-patchoulene, $\beta$-patchoulene, $\alpha$-bulnesene, seychellene, norpatchoulenol, pogostone, eugenol and pogostol. The non-volatiles include acacetin, apigenin, licochalcone A, ombuin, rhamnetin, retusine, acteoside, agastachoside, isocrenatoside, tilianin, rubusoside, tri- and sesquiterpenes.

Patchouli is used widely in fine fragrance and perfumery, and it is an important ingredient in East Asian incense. Patchouli leaves have been used to make an herbal tea. In some cultures, patchouli leaves are eaten as a vegetable or used as a seasoning. Patchouli has also been described as an insect repellent, in against the Formosan subterranean termite.

It is an aim of the present invention to add value to the Patchouli stems that have been used for Patchouli oil production.

This is achieved by the cosmetic compositions and methods of the present invention.

In a first aspect, the present invention provides a cosmetic composition comprising a carrier and at least one active cosmetic ingredient, wherein a first active cosmetic ingredient comprises a Patchouli stem extract.

In contrast to the essential oil obtained by hydrodistillation or steam distillation, the Patchouli stem extract is obtained by extracting the Patchouli stems with a liquid solvent.

The Patchouli stem extract of the present invention is fully natural and odour-free.

Surprisingly, it was found that the Patchouli stem extract of the present invention possesses impressive skin care and anti-aging properties.

In particular, it was found to exhibit antioxidant, anti-elastase, anti-hyaluronidase, and anti-tyrosinase activities.

Therefore, in a particular embodiment, the cosmetic composition of the present invention is a skin care composition, in particular an anti-ageing composition. To this end, the carrier should be a dermatologically acceptable carrier.

A particularly suitable extract is an aqueous extract of Patchouli stems. Therefore, in a preferred embodiment of the present invention, the first active cosmetic ingredient comprises an aqueous extract of Patchouli stems.

Another particularly suitable extract is an alcoholic extract of Patchouli stems. Therefore, in a preferred embodiment of the present invention, the first active cosmetic ingredient comprises an alcoholic extract of Patchouli stems. Ethanol is a particularly preferred solvent.

In a particularly preferred embodiment, the Patchouli stems—and in particular the exhausted Patchouli stems—are extracted with an alcohol-water mixture. Ethanol-water mixtures are especially suitable.

The aqueous extract may be obtained by extracting Patchouli stems with pure water. Optionally, the water may contain additives, e.g. for adjusting the pH.

Surprisingly, it was found that even the extraction of exhausted Patchouli stems provided an active cosmetic ingredient having the advantageous effects described above. Therefore, in a particular embodiment of the present invention, the first active cosmetic ingredient comprises an extract of exhausted Patchouli stems.

Throughout this application, the term "exhausted Patchouli stems" refers to Patchouli stems that have previously been processed by steam distillation. Thus, it refers to the remains of the root after the essential oil has been removed.

In a particular embodiment, the invention relates to an aqueous and/or alcoholic extract of exhausted Patchouli stems. This allows for adding additional value to a "waste" product.

In a further aspect, the present invention relates to a method of preparing an active cosmetic ingredient, the method comprising extracting Patchouli stems.

By extracting, it is meant that the Patchouli stems are treated with a solvent or a mixture of solvents. The solvent(s) may also contain additives. For instance, the Patchouli stems may be subjected to water extraction, acidic extraction, enzymatic extraction, ultrasound assisted water extraction, pressurized water extraction or ethanolic extraction.

Preferably, the Patchouli stems are reduced to smaller pieces prior to the extraction, in particular cut and/or ground.

The Patchouli stems may also be washed prior to the extraction. It was found that washing the stems, in particular with water, led to a decreased color of the extract.

The Patchouli stems are preferable extracted with water, ethanol or mixtures thereof.

It was found that extraction with 70% ethanol in water, optionally containing one or more additives, provides the best results.

Suitable additives include, but are not limited to, acids, base, buffers, salts and/or co-solvents. In particular, the pH of the extraction solvent may be adjusted by the addition of acid (e.g. $H_2SO_4$ or citric acid) or base (e.g. NaOH).

The extraction may be performed at room temperature or at elevated temperature, e.g. at a temperature of about 40° C., about 60° C., or about 80° C.

The Patchouli stem extract may be purified, for example by filtration (e.g. on KDS15 filters), charcoal treatment and/or sterilizing filtration.

The Patchouli stem extract may also be concentrated. It is possible to add a solvent, e.g. 1,3-propanediol, to the extract prior to concentration to improve the solubility of the extract during concentration.

In a particular embodiment, the method of the present invention comprises the steps of (i) providing exhausted Patchouli stems; and (ii) extracting the exhausted Patchouli stems.

Thus, in conclusion, the composition of the present invention provides a stimulation of sebum production, a stimulation of antioxidant property and a strong inhibition of wound healing through a control of keratinocytes migration.

Therefore, the composition of the present invention may be used in skin care, scalp care and/or body care compositions, in particular in serums for dry skin, anti-aging serums, anti-aging night and day creams, anti-dry dandruff products, dry scalp lotions or body care lotions.

In a further aspect, the present invention relates to the use of an extract from Patchouli stems in skin care. This allows for exploiting the positive effects of the Patchouli stem extract described above.

In a particular embodiment, an aqueous extract and/or an extract from exhausted Patchouli stems is used.

The Patchouli stem extract is particularly advantageously used in an anti-aging product, an anti-dandruff product, or a product for dry skin and/or scalp.

In a further aspect, the present invention relates to a method of stimulating the sebum production, of stimulating the antioxidant property and/or of inhibiting wound healing by applying the cosmetic composition of the present invention to human skin.

The present invention is further illustrated by means of the following non-limiting examples:

Example 1: Preparation of Patchouli Stem Extract

Dried hydrodistilled Patchouli stems were crushed to obtain a powder. 25 g of powder were extracted at room temperature in 500 g of ethanol (70% in water) for 30 min under stirring. The extract (around 420 g) was filtered over an Eaton KDS15 filter (123 cm²). The filtrate was concentrated by a factor of 5.2 by evaporation under vacuum to obtain about 80 g of concentrated product.

One batch of the concentrated product (Batch A) was used as such. This non decolorized product was black.

A second batch of the concentrated product (Batch B) was decolorized on charcoal filters (24 cm²). This decolorization process efficiently decreased colour. It decreased dry matter around 2 fold.

The two batches were finally filtered over an Eaton S60 filter (24 cm²) and sterile PES filtration unit (VWR) to store the final products without preservatives.

The characteristics of the two batches are shown in the following table:

| | Amount of final product | Dry matter content | Gardner | pH |
|---|---|---|---|---|
| Batch A | 56 g | 3.80% | 15.2 | 5.1 |
| Batch B | 40 g | 1.57% | 5.6 | 4.6 |

-continued

| | Amount of final product | Dry matter content | Gardner | pH |
|---|---|---|---|---|

For comparison of different solvents, extractions were also performed with water, 100% ethanol, ethanol 70% and ethanol 50%. Color (Gardner) and dry matter content were measured on raw extracts. The results are shown below:

| | Water | 50% Ethanol | 70% Ethanol | 100% Ethanol |
|---|---|---|---|---|
| Gardner | 8.0 | 9.0 | 8.5 | 5.6 |
| Dry matter content | 0.52% | 0.53% | 0.54% | 0.0% |

Essentially no difference of color or even dry matter content was observed (except for 100% ethanol), but the yield in dry matter was in general very low.

Example 2: Analysis of Patchouli Stem Extract

Dried hydrodistilled Patchouli stems were crushed to obtain a powder. 75 g of powder were extracted at 20° C. in 550 g of ethanol (70% in water) for 60 min under stirring. Extract was filtered through a 0.7 μm cellulosic filter, concentrated five times to remove ethanol and finally filtered through a 0.35 μm cellulosic filter. The extract was then freeze dried.

Fractionation of the Crude Extract by Centrifugal Partition Chromatography (CPC)

The crude extract (1.078 g) was dissolved in 30 ml a biphasic solvent system consisting of methyl-tert-butylether (MTBE), acetonitrile and water in a 3:3:4 ratio (v/v). Centrifugal Partition Chromatography (CPC) was performed using an FCPE300® instrument (Rousselet Robatel Kromaton) with a column of 303 ml, a column rotation speed of 1200 rpm and a flow rate of 20 ml/min.

An isocratic elution of the mobile phase (lower phase of the two-phase solvent system) was performed in the ascending mode for 75 min (with an initial flow rate ramp from 0 to 20 ml/min during 5 min). The column was finally extruded by switching the mode selection valve for 20 min. The CPC chromatogram was monitored at 220 nm. Fractions of 20 ml were collected over the whole experiment, and combined according to their thin layer chromatography (TLC) profiles. TLC was performed on pre-coated silica gel 60 F254 Merck plates with the migration solvent system EtOAc/toluene/formic acid/acetic acid (70/30/11/11; v/v), visualized under UV light at 254 nm and 360 nm and revealed by spraying the dried plates with 50% $H_2SO_4$ and vanillin followed by heating. As a result, 16 sub-fractions were collected.

NMR Analyses and Identification of the Major Metabolites

An aliquot of each fraction from F1 to F16 (up to ≈20 mg) was dissolved in 700 μl DMSO-d6 and analyzed by $^{13}$C NMR at 298 K on a Bruker Avance AVIII-600 spectrometer (Karlsruhe, Germany) equipped with a TXI cryoprobe. Spectra were manually phased and baseline corrected using the TOPSPIN 3.2 software (Bruker) and calibrated on the central resonance of DMSO-d6 (δ 39.80 ppm). The absolute intensities of all $^{13}$C NMR signals were automatically collected and binned across the spectra of the fraction series by using a locally developed computer script. The resulting table was imported into the PermutMatrix version 1.9.3 software (LIRMM, Montpellier, France) for Hierarchical Clustering Analysis (HCA). The resulting $^{13}$C chemical shift clusters were visualized as dendrograms on a two-dimensional map. For metabolite identification, each $^{13}$C chemical shift cluster obtained from HCA was manually submitted to the structure search engine of the database management software ACD/NMR Workbook Suite 2012 software, ACD/Labs, Ontario, Canada) comprising the structures and predicted chemical shifts of low molecular weight natural products (n 2950 in March 2018). In parallel, a literature survey was performed to obtain the names and chemical structures of a maximum of metabolites already reported in the species *Pogostemon cablin* (n≈70). Additional 2D NMR Protocatechuic acid
Syringaresinol
Vanillin
Rhamnocitrin
Luteolin-7-O-glucuronide
Hydroxymethylglutaric acid
12-hydroxyjasmonic acid
a caffeoyl derivate
apigenin-7-sugars The composition of the CPC fractions was as follows (Maj=major; Med=medium; Min=minor):

| CPC-Fractions | Mass (mg) | % crude extract | Composition |
|---|---|---|---|
| 1 Elution | 7.9 | 0.7 | 7',3'-dimethyleriodictyol (Maj); Pachypodol (Maj); Rhamnocitrin (Min) |
| 2 Elution | 16.7 | 1.5 | 7',3'-dimethyleriodictyol (Maj); Pachypodol (Maj); Cytosporone V (Med); Rhamnocitrin (Min) |
| 3 Elution | 7.7 | 0.7 | p-hydroxybenzoic acid (Maj); Syringaresinol (Min); Vanillin (Med) |
| 4 Elution | 10.2 | 0.9 | Protocatechuic acid (Maj); Syringaresinol (Min); Vanillin (Med) |
| 5 Elution | 14.0 | 1.3 | 12-hydroxyjasmonic acid (Maj) + caffeoyl derivatives and Apigenin-7-sugars |
| 6 Elution | 11.8 | 1.1 | Apigenin-7-O-glucuronide (Min); Succinic acid (Min); caffeoyl derivatives and Apigenin-7-sugars |
| 7 Elution | 10.6 | 1.0 | Verbascoside (Min); Apigenin-7-O-glucuronide (Maj); Succinic acid (Maj); Glucosyl-cytosporone V (Min) |
| 8 Elution | 16.0 | 1.5 | Verbascoside (Med); Apigenin-7-O-glucuronide (Med); Succinic acid (Maj); Glucosyl-cytosporone V (Min) |
| 9 Elution | 26.7 | 2.5 | Verbascoside (Maj); Apigenin-7-O-glucuronide (Min); Succinic acid (Med); Glucosyl-cytosporone V (Med); Luteolin-7-O-glucuronide (Min) |
| 10 Elution | 26.9 | 2.5 | Verbascoside (Maj); Apigenin-7-O-glucuronide (Min); Succinic acid (Min); Glucosyl-cytosporone V (Med); Luteolin-7-O-glucuronide (Min); Hydroxymethylglutaric acid (Med) |
| 11 Elution | 56.0 | 5.2 | Apigenin-7-O-glucuronide (Min); Succinic acid (Min); Lactic acid (Maj); Luteolin-7-O-glucuronide (Min); Hydroxymethylglutaric acid (Maj) |
| 12 Extrusion | 97.5 | 9.0 | Choline (Min); α-D-fructose (Min); β-D-fructose (Med); α-D-glucose (Maj); α-D-glucose (Maj); β-D-fructopyranose (Min) |
| 13 Extrusion | 329.4 | 30.3 | Choline (Min); α-D-fructose (Med); β-D-fructose (Maj); α-D-glucose (Maj); β-D-glucose (Maj); β-D-fructopyranose (Med) |
| 14 Extrusion | 306.0 | 28.2 | Choline (Min); α-D-fructose (Med); β-D-fructose (Maj); α-D-glucose (Maj); β-D-glucose (Maj); β-D-fructopyranose (Med) |
| 15 Extrusion | 68.0 | 6.3 | Choline (Min); α-D-fructose (Med); β-D-fructose (Maj); α-D-glucose (Maj); β-D-glucose (Maj); β-D-fructopyranose (Med) |
| 16 Extrusion | 81.1 | 7.5 | Choline (Min); α-D-fructose (Min); β-D-fructose (Med); α-D-glucose (Med); β-D-glucose (Med); β-D-fructopyranose (Min) | experiments (HSQC, HMBC, and COSY) were performed on fractions containing putatively identified compounds in order to confirm the molecular structures proposed by the database at the end of the dereplication process.

The following major metabolites were identified:
Verbascoside
Apigenin-7-O-glucuronide
Succinic acid
Glucosyl-cytosporone V (2 isomers)
Lactic acid
Choline
α-D-fructose
β-D-fructose
α-D-glucose
β-D-glucose
β-D-fructopyranose
7,3'-dimethyleriodictyol
Pachypodol
Cytosporone V
p-hydroxybenzoic acid Example 3: Screening of Biological Activity The two batches A and B from Example 1 were tested for antioxidant (DPPH), anti-elastase, anti-hyaluronidase, and anti-tyrosinase activities. Results are presented in the following table:

| IC50 | DPPH | Elastase | Hyaluronidase | Tyrosinase |
|---|---|---|---|---|
| Batch A | 0.07 mg/ml | 16.60 mg/ml | 37.38 mg/ml | 6.11 mg/ml |
| Batch B | 0.20 mg/ml | n.a. | n.a. | 9.53 mg/ml |

The non-decolorized Batch A clearly presented high biological activities.

The decolorized Batch B only displayed a slight antioxidant activity, but similar anti-tyrosinase activity as Batch A.

Example 4: Wound Healing

Normal Human Keratinocytes (NHEKs) were seeded at 200'000 cells per well pre-coated with Type I collagen in 12-wells culture plates in the presence of keratinocyte growth medium (KGM, Lonza) supplemented with growth factors such as hydrocortisone, transferrin, epinephrine, bovine pituitary extract (BPE), recombinant human epidermal growth factor (rhEGF) and insulin. At confluence, cells were pre-incubated with the Patchouli stem extract of Example 1 at a concentration of 0.5% (v/v) or heparin-binding epidermal growth factor (HB-EGF) at 1 ng/ml (positive control) overnight in keratinocyte basal medium without supplement. After this pre-conditioning phase, the cell monolayer sticking to the bottom of the well was scratched with a P200 sterile cone, followed by two washes with phosphate buffered saline (PBS). The NHEK were then again stimulated with Patchouli extract at 0.5% or HB-EGF at 1 ng/ml for 8 h in basal medium.

The wound healing process was analyzed by pictures recording at $T_0$ and $T_{8h}$ using inverting optical microscope (Zeiss). After image analysis, the percentage of scratch closing was determined relative to untreated condition.

It was found that the Patchouli stem extract significantly inhibited wound healing by about −50% in the NHEK scratch assay, while HB-EGF led to an enhancement by about +60%. An inhibition of wound healing is particularly important in conditions involving a hyperproliferation of keratinocytes, e.g. hyperkeratosis or dry dandruff.

Example 5: Anti-Oxidant Activity

NHEKs were seeded in a black plate with a glass bottom at 20'000 cells per well pre-coated with type I collagen. Cells were incubated at 37° C. with 5% $CO_2$ for 24 h. On the next day, the cells were incubated for 24 h with the Patchouli stem extract of Example 1 at a concentration of 0.5% (v/v) or Resveratrol (positive control) at 200 μM. After this pre-incubation, the cells were incubated with dichloro-di-hydro-fluorescein (DCFH) probe at 50 μM for 30-45 min. The cells were then rinsed two times with PBS and incubated with PBS alone or with PBS containing 5 mM tert-butyl peroxide (TBP) to induce an oxidative stress. Fluorescence reading was performed every 10 min for 1 h, exciting at 488 nm and emitting at 525 nm.

It was found that the Patchouli stem extract led to a reduction in reactive oxygen species (ROS) production by −28%, evidencing anti-oxidant properties.

Example 6: Regulation of Sebum Production

Human sebocytes were seeded in 96-wells plates (50'000 cells/well) and cultured for 24 h in keratinocyte serum free medium (SFM) supplemented with gentamycin at 25 μg/ml. The culture medium was then remove and replaced by the Patchouli stem extract of example 1 at a concentration of 1% (v/v) or the reference, olumacostat glasaretil at 1 μM. The cells were pre-incubated for 4 h. Then, a lipogenic mix containing vitamin C, vitamin D3, insulin and calcium (without androgens) was added and the cells were incubated for 7 days. After 3 days of incubation, half of the culture medium was removed and the treatments were renewed (including lipogenic mix stimulation). A non-stimulated control condition was performed in parallel. At the end of the incubation, the cells were rinsed, fixed and permeabilized. The lipid droplets contained in the cells were then labeled using a specific Bodipy® fluorescent lipid probe labelling mainly neutral lipids. In parallel, the cell nuclei were stained using a Hoechst 33258 solution. The acquisition of the images was performed using INCell Analyzer™ 2200. Five photos were taken per well (×20 objective lens). The labelling was quantified by fluorescence intensity measurement normalized to the total number of cells.

It was found that the Patchouli stem extract significantly induced the sebum production from sebocytes under lipogenic stimulation by +39%. A stimulation of sebum production is particularly useful in the treatment of dry skin and for restoring the skin barrier and skin permeability.

The invention claimed is:

1. A cosmetic composition comprising a carrier and at least one active cosmetic ingredient, wherein the at least one active cosmetic ingredient comprises an aqueous extract or an aqueous and alcoholic extract of exhausted Patchouli stems, wherein Patchouli stems comprising essential oil have previously been processed by steam distillation to provide the exhausted Patchouli stems, wherein the exhausted Patchouli stems consist of remains after the essential oil has been removed.

2. The cosmetic composition of claim 1, wherein the cosmetic composition is a skin care, scalp care or body care composition.

3. The cosmetic composition of claim 2, wherein the cosmetic composition is a serum for dry skin, an anti-aging serum, an anti-aging night or day cream, an anti-dry dandruff product, a dry scalp lotion or is a body care lotion.

4. The cosmetic composition of claim 1, wherein the aqueous extract or the aqueous and alcoholic extract of exhausted Patchouli stems is odour-free.

5. A method of preparing an active cosmetic ingredient, comprising the step of:
extracting exhausted Patchouli stems using either water or water and alcohol to provide an aqueous extract or an aqueous and alcoholic extract of exhausted Patchouli stems as the active cosmetic ingredient, wherein Patchouli stems comprising essential oil have previously been processed by steam distillation to provide the exhausted Patchouli stems, wherein the exhausted Patchouli stems consist of remains after the essential oil has been removed.

6. A method of treating human skin, comprising the step of:
applying an aqueous extract or an aqueous and alcoholic extract of exhausted Patchouli stems onto human skin, wherein Patchouli stems comprising essential oil have previously been processed by steam distillation to provide the exhausted Patchouli stems, wherein the exhausted Patchouli stems consist of remains after the essential oil has been removed.

7. A method of stimulating sebum production, of stimulating an antioxidant property and/or of inhibiting wound healing, the method comprising the step of: applying the cosmetic composition of claim 1 to human skin.

* * * * *